(12) United States Patent
Nasu et al.

(10) Patent No.: US 10,088,666 B2
(45) Date of Patent: Oct. 2, 2018

(54) ENDOSCOPE AND VARIABLE POWER OPTICAL SYSTEM FOR THE SAME

(71) Applicant: HOYA CORPORATION, Tokyo (JP)

(72) Inventors: Sachiko Nasu, Tokyo (JP); Hiroaki Fujii, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 215 days.

(21) Appl. No.: 15/304,274

(22) PCT Filed: Feb. 23, 2016

(86) PCT No.: PCT/JP2016/055250
§ 371 (c)(1),
(2) Date: Oct. 14, 2016

(87) PCT Pub. No.: WO2017/145264
PCT Pub. Date: Aug. 31, 2017

(65) Prior Publication Data
US 2018/0017779 A1    Jan. 18, 2018

(51) Int. Cl.
G02B 23/24     (2006.01)
G02B 15/177    (2006.01)
A61B 1/00      (2006.01)

(52) U.S. Cl.
CPC ........ G02B 23/2438 (2013.01); A61B 1/0019 (2013.01); G02B 15/177 (2013.01)

(58) Field of Classification Search
CPC .. G02B 23/2438; G02B 15/177; A61B 1/0019
(Continued)

(56) References Cited

U.S. PATENT DOCUMENTS 7,145,732 B2    12/2006   Matsusaka et al.
7,292,395 B2    11/2007   Noda
(Continued)

FOREIGN PATENT DOCUMENTS

JP    2005-292403 A    10/2005
JP    2007-93961 A     4/2007
(Continued)

OTHER PUBLICATIONS

International Search Report, along with English-language translation thereof, for PCT/JP2016/055250 dated May 24, 2016.
(Continued)

*Primary Examiner* — Jie Lei
*Assistant Examiner* — Mitchell Oestreich
(74) *Attorney, Agent, or Firm* — Greenblum & Bernstein, P.L.C.

(57) ABSTRACT

A variable power optical system for an endoscope comprising a first lens group having a negative power, a second lens group having a positive power and a third lens group, and wherein the first lens group includes at least a negative lens having a concave surface pointing to an image side and a positive meniscus lens having a concave surface pointing to an object side, the second lens group includes at least a meniscus lens having a convex surface pointing to the object side and a cemented lens formed by cementing together a negative lens and a positive lens, and the third lens group includes at least a positive lens having a convex surface pointing to the object side, and wherein the variable power optical system for an endoscope is configured to satisfy a predetermined condition.

8 Claims, 11 Drawing Sheets

(58) Field of Classification Search
USPC .......................................................... 359/689
See application file for complete search history.

(56) References Cited

U.S. PATENT DOCUMENTS

| | | |
|---|---|---|
| 8,203,798 B2 | 6/2012 | Takato |
| 9,110,302 B2 | 8/2015 | Katakura |
| 2010/0142058 A1* | 6/2010 | Takato ................. G02B 23/243 |
| | | 359/661 |

FOREIGN PATENT DOCUMENTS

| | | |
|---|---|---|
| JP | 4819969 B2 | 11/2011 |
| JP | 2014-145869 A | 8/2014 |
| JP | 5580956 B1 | 8/2014 |

OTHER PUBLICATIONS

Written Opinion of the International Searching Authority, for PCT/JP2016/055250 dated Aug. 31, 2017.

* cited by examiner

ENDOSCOPE AND VARIABLE POWER OPTICAL SYSTEM FOR THE SAME

TECHNICAL FIELD

The present invention relates a variable power optical system for an endoscope and an endoscope provided with such a variable power optical system.

BACKGROUND ART

In a medical field, an endoscope (a fiber scope or an electronic scope) is generally known as a device for observing a body cavity of a patient and has been practically used. Among endoscopes of this type, there is an endoscope provided with a variable power optical system having the variable power function for conducting fine observation for lesions.

For example, Japanese Patent Publication No. JP4819969B (hereafter, referred to as a "patent document 1") describes a concrete configuration of a variable power optical system for an endoscope. The variable power optical system for an endoscope described in the patent document 1 includes a first lens group having a negative power, a second lens group having a positive power and a third lens group having a positive power which are arranged in this order from the object side, and is configured to perform focusing by moving the second lens group in accordance with change of the object distance without changing the entire length defined as a distance from the first lens group to the image plane.

SUMMARY OF THE INVENTION

However, a lens configuration of a negative-leading type (a type in which a most object side lens is a negative lens) exemplified in the patent document 1 has a drawback that the effective diameter of the most object side negative lens needs to be increased to suppress occurrence of aberrations while securing an angle of view at the wide angle end. A variable power optical system of such a negative-leading type decreases a degree of freedom regarding disposing of components (e.g., a light guide, a forceps, an air supply or water supply channel) to be installed in a tip portion of an endoscope, and is hard to be installed in a fine tip portion of an endoscope. Furthermore, in the lens configuration exemplified in the patent document 1, a degree of change of power is small although focusing can be achieved in response to change of the object distance. Furthermore, since fluctuation of aberration becomes larger when the observing magnification is changed, it is difficult to keep the adequate optical performance over the entire region from the wide angle end to the telephoto end.

The present invention is made in view of the above described circumstances. That is, the object of the present invention is to provided an endoscope and a variable power optical system for an endoscope capable of suppressing the size in a radial direction even if a lens configuration is the negative-leading type, capable of keeping the adequate optical performance over the entire region from the wide angle end to the telephoto end, and capable of securing an adequate observing magnification.

A variable power optical system for an endoscope according to an embodiment of the invention comprises a first lens group having a negative power, a second lens group having a positive power and a third lens group arranged in this order from an object side. The variable power optical system for an endoscope is configured to change magnification for an optical image by moving the second lens group in a direction of an optical axis with respect to the first lens group and the third lens group which are fixed lens groups, while keeping a distance from a most object side lens surface of the first lens group to an image plane constant. The first lens group includes at least a negative lens having a concave surface pointing to an image side and a positive meniscus lens having a concave surface pointing to the object side, arranged in this order from the object side. The second lens group includes at least a meniscus lens having a convex surface pointing to the object side and a cemented lens formed by cementing together a negative lens and a positive lens, arranged in this order from the object side. The third lens group includes at least a positive lens having a convex surface pointing to the object side.

When a focal length of the meniscus lens which the first lens group includes is defined as $f_{s1}$ (unit: mm), an overall focal length of the first to third lens groups at a wide angle end is defined as $f_w$ (unit: mm), and the overall focal length of the first to third lens groups at a telephoto end is defined as $f_t$ (unit: mm), the variable power optical system for an endoscope according to an embodiment of the invention satisfies following two conditions:

$$20 < f_{s1}/f_w < 50$$

$$1.2 < f_t/f_w < 1.5.$$

When a focal length of the first lens group is defined as $f_1$ (unit: mm), the above described condition ($20 < f_{s1}/f_w < 50$) may be replaced with the following condition:

$$5 < |f_{s1}/f_1| < 20.$$

When a focal length of the second lens group is defined as $f_2$ (unit: mm), the variable power optical system for an endoscope according to an embodiment of the invention may be configured to satisfy the following condition:

$$2 < f_2/f_w < 5.$$

When a focal length of the third lens group is defined as $f_3$ (unit: mm), the variable power optical system for an endoscope according to an embodiment of the invention may be configured to satisfy the following condition:

$$5 < f_3/f_w < 20.$$

When a focal length of the first lens group is defined as $f_1$ (unit: mm), the variable power optical system for an endoscope according to an embodiment of the invention may be configured to satisfy the following condition:

$$-4 < f_1/f_w < -2.$$

The variable power optical system for an endoscope according to an embodiment of the invention may further comprise an aperture stop disposed between the first lens group and the second lens group to move along the optical axis integrally with the second lens group.

In the variable power optical system for an endoscope according to an embodiment of the invention, an angle of view of the variable power optical system for an endoscope is, for example, 120 degrees or more.

An endoscope according to an embodiment of the invention comprises the above described variable power optical system for an endoscope installed in a tip portion of the endoscope.

According to the embodiments of the invention, an endoscope and a variable power optical system for an endoscope capable of suppressing the size in a radial direction even if a lens configuration is the negative-leading type, capable of keeping the adequate optical performance over the entire region from the wide angle end to the telephoto end, and capable of securing an adequate observing magnification are provided.

EMBODIMENTS FOR CARRYING OUT THE INVENTION

In the following, explanation is given for a variable power optical system for an endoscope according to an embodiment of the invention and an electronic scope in which such a variable power optical system for an endoscope is installed, with reference to the accompanying drawings.

Figure 1:
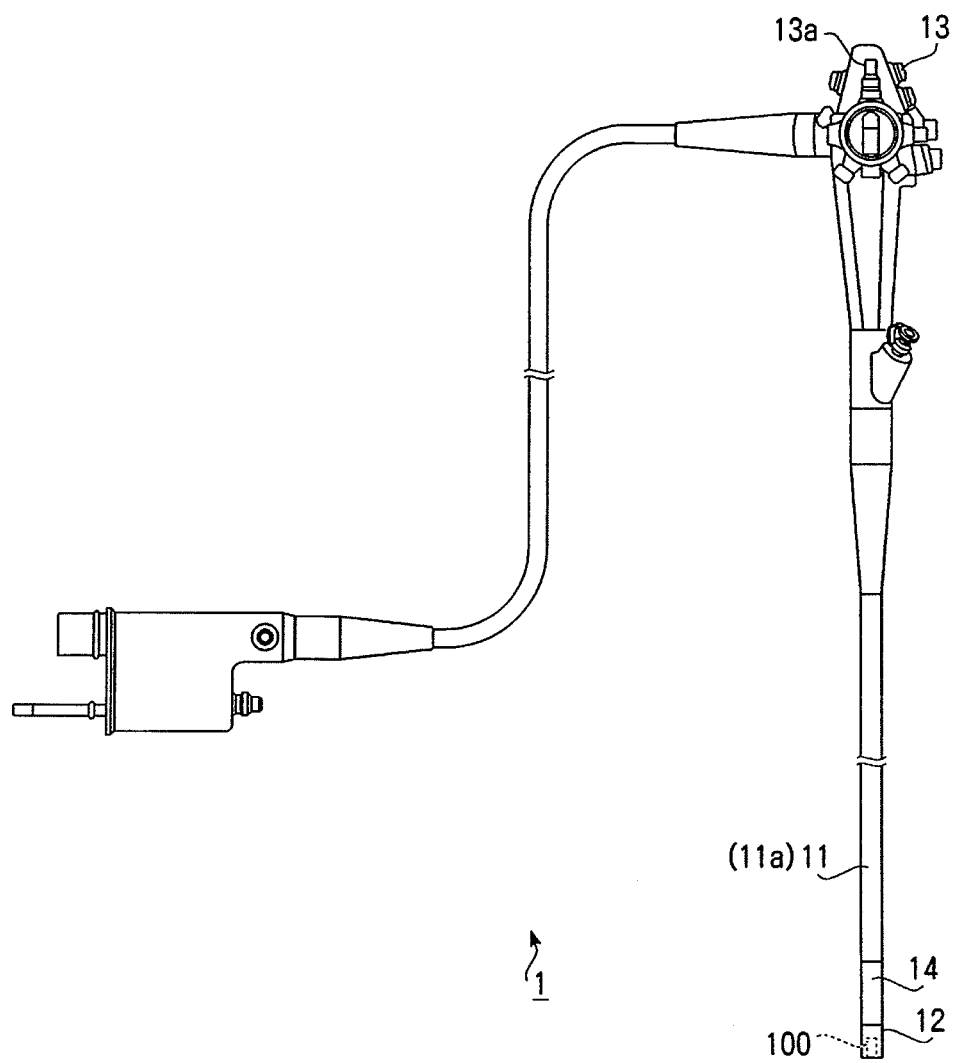
FIG. 1 is an external view illustrating an outer appearance of an electronic scope according to an embodiment of the invention.

FIG. 1 is an external view illustrating an outer appearance of an electronic scope 1 according to the embodiment of the invention. As shown in FIG. 1, the electronic scope 1 includes an elastic insertion tube 11 covered with a sheath 11a having elasticity. A tip portion (a bending part 14) of the elastic insertion tube 11 is configured to be bent in response to remote control (specifically, a rotating operation for a bending operation knob 13a) from a hand operating unit 13 coupled to the proximal end of the elastic insertion tube 11. A mechanism for such bending is a known mechanism installed in a general endoscope, and is configured to bend the bending part 14 through drawing of operation wires in conjunction with the rotating operation for the bending operation knob 13a. To a tip of the bending part 14, the proximal end of a tip portion 12 covered with a resin housing having rigidity is connected. In response to change of the direction of the tip portion 12 due to the bending motion caused by the rotating operation for the bending operation knob 13a, an imaging area of the electronic scope 1 moves.

In the inside of the resin housing of the tip portion 12, a variable power optical system 100 for an endoscope (a block indicated by a dashed line in FIG. 1) is installed. The variable power optical system 100 for an endoscope converges light from a subject onto a light-receiving surface of a solid-state image pickup device (not shown) so as to pick up image data of the subject in the imaging area. As the solid-state image pickup device, a CCD (Changed Coupled Device) image sensor or a CMOS (Complementary Metal Oxide Semiconductor) image sensor may be used.

Figure 2:
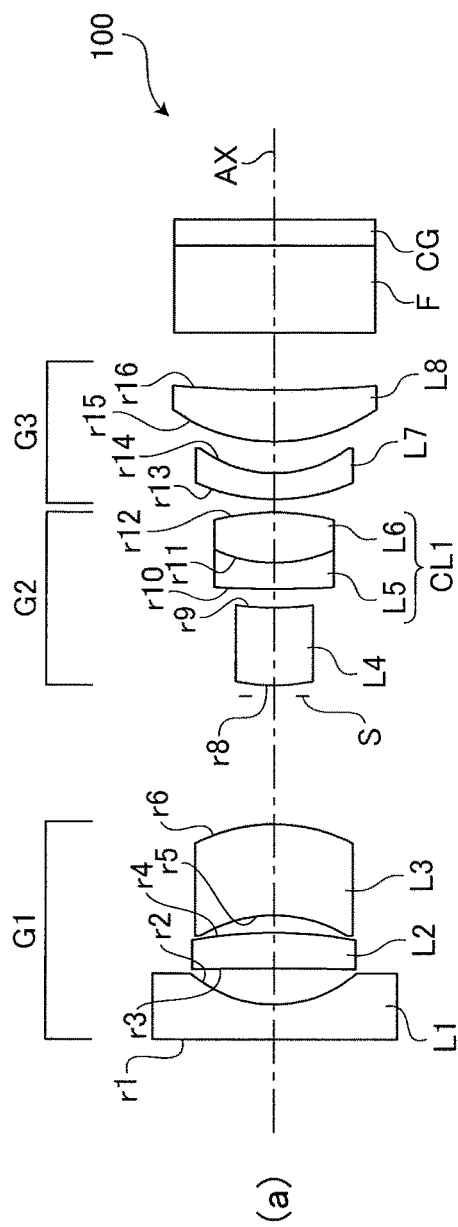
FIG. 2 is a lens arrangement diagram illustrating a configuration of a variable power optical system for an endoscope according to an example 1 of the invention.
Figure 2:
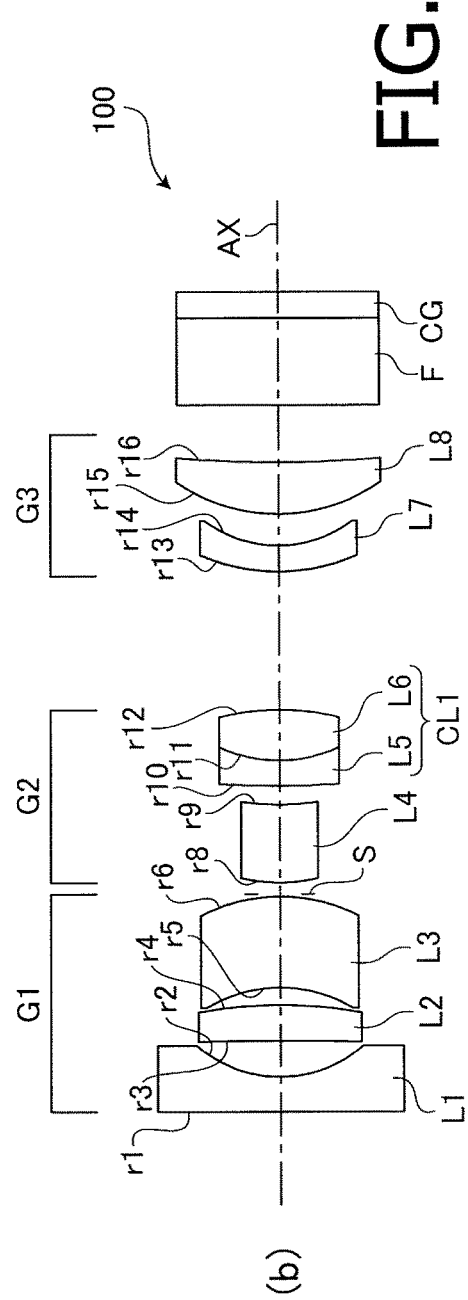

FIG. 2 is a cross sectional view illustrating disposition of the variable power optical system 100 for an endoscope and optical components disposed on the rear side of the variable power optical system 100 for an endoscope, according to an example 1 of the invention (which is described in detail later). FIGS. 2(a) and 2(b) illustrate lens arrangements when the position of the variable power is at the wide angle end and the telephoto end, respectively. In the following, the variable power optical system 100 for an endoscope according to the embodiment of the invention is explained in detail with reference to FIG. 2.

As shown in FIG. 2, the variable power optical system 100 for an endoscope includes a first lens group G1 having a negative power, an aperture stop S, a second lens group G2 having a positive power and a third lens group G3 having a positive power or a negative power. The variable power optical system 100 for an endoscope is configured to change the overall focus length (i.e., a combined focus length defined from the first lens group G1 to the third lens group) while keeping the focused state and thereby to change magnification for an optical image, by letting the second lens group G2 move in an optical axis AX direction with respect to the first lens group G1 and the third lens group G3 which are fixed lens groups, while keeping the distance (i.e., the entire length of the variable power optical system 100 for an endoscope) from the most object side lens surface of the first lens group G1 to the image plane constant. The variable power optical system 100 for an endoscope has the angle of view of 120 degrees or more (the half angle of view of 60 degrees or more) at the wide angle end. Each optical lens constituting each of the first to third lens groups G1 to G3 has a rotationally-symmetrical shape about the optical axis AX. On the rear side of the third lens group G3, a color correction filter F for the solid-state image pickup device is disposed. The color correction filter F is adhered to a cover glass CG for protecting the solid-state image pickup device.

The first lens group G1 includes at least a negative lens having a concave surface pointing to the image side (a lens L1 in the example shown in FIG. 2), a positive meniscus lens having a concave surface pointing to the object side (a lens L3 in the example shown in FIG. 2) which are arranged in this order from the object side. The first lens group G1 is a lens group having a negative power disposed on the object side with respect to the aperture stop S. The expression "includes at least" used above means that a lens group may be additionally provided with another optical component, such as a parallel plate, within the scope of the present invention. For the same reasons, the expression "includes at least" is also used in explanations about the second lens group G2 and the third lens group G3.

By thus disposing, in the first lens group G1, a meniscus lens which has a concave surface pointing to the object side (in other words, which has a convex surface pointing to the image side) and has a positive power, aberrations caused by the negative lens having the concave surface pointing to the image side can be canceled out. As a result, fluctuation of the aberrations in the entire optical system can be suppressed, and thereby the adequate optical performance can be maintained over the entire region from the wide angle end to the telephoto end.

The second lens group G2 is a lens group which is disposed on the rear side of the aperture stop S and has a positive power. In order to suppress occurrence of chromatic aberration, the second lens group G2 is configured to include, in the order from the object side, at least a meniscus lens (a lens L4 in the example shown in FIG. 2) having a convex surface pointing to the object side, and a cemented lens (a cemented lens CL1 formed by cementing together a lens L5 and a lens L6) formed by cementing together positive and negative two lenses. In the example shown in FIG. 2, the cemented lens CL1 is formed by disposing the negative lens (the lens L5) on the object side and disposing the positive lens (the lens L6) on the image side; however, in another embodiment the cemented lens may be configured by disposing a positive lens on the object side and disposing a negative lens on the image side.

The second lens group G2 moves integrally with the aperture stop S in the optical axis AX direction in order to change magnification for the optical image formed on the light-receiving surface of the solid-state image pickup device. By moving the second lens group G2 together with the aperture stop S, astigmatism caused at the telephoto end can be effectively suppressed.

The aperture stop S may be a plate-like member having a circular hole centered at the position of the optical axis AX or may be a light shielding film which is formed on a lens surface (an object side surface r8 in the example shown in FIG. 2) nearest to the aperture stop S in the second lens group G2 to coating a region other than a circular region centering at the position of the optical axis AX. The thickness of the aperture stop S is extremely small relative to the thickness of each lens constituting the variable power optical system 100 for an endoscope, and may be neglected when the optical performance of the variable power optical system 100 for an endoscope is calculated. Therefore, in the following, explanation is given assuming that the thickness of the aperture stop S is zero.

The third lens group G3 is a lens group having a positive or negative power, and includes at least a positive lens (a lens L8 in the example shown in FIG. 2) having a convex surface pointing to the object side, in order to suppress the exit angle of light proceeding from the variable power optical system 100 for an endoscope to the solid-state image pickup device.

When the focal length of the meniscus lens of the first lens group G1 is defined as $f_{s1}$ (unit: mm), the overall focal length at the wide angle end is defined as $f_w$ (unit: mm), and the overall focal length at the telephoto end is defined as $f_t$ (unit: mm), the variable power optical system 100 for an endoscope is configured to satisfy the following conditions (1) and (2):

$$20 < f_{s1}/f_w < 50 \quad (1)$$

$$1.2 \leq f_t/f_w < 1.5 \quad (2)$$

By satisfying the condition (1), it becomes possible to suppress the effective diameter of the negative lens in the first lens group G1 which has the greatest tendency to become large in the variable power optical system 100 for an endoscope, and thereby it becomes possible to suppress the size in the radial direction of the entire variable power optical system 100 for an endoscope. Therefore, the variable power optical system 100 for an endoscope is suitable for installing into the inside of the tip portion 12 of the electronic scope 1 designed to have a small diameter. Furthermore, since the size in the radial direction of the entire variable power optical system 100 for an endoscope is suppressed, a degree of freedom regarding disposing of other components (e.g., a light guide, a forceps, an air supply or water supply channel) to be installed into the tip portion 12 is enhanced.

Furthermore, by satisfying the condition (1), aberrations caused in the first lens group G1 can be suppressed, and thereby it becomes possible to more suitably maintain the suitable optical performance over the region from the wide angle end to the telephoto end.

When, regarding the condition (1), $f_{s1}/f_w$ gets larger than or equal to 50 (the value of the right term), the positive power in the first lens group G1 becomes too small and thereby it becomes difficult to cancel out the aberration caused by the negative lens in the first lens group G1. Furthermore, when, regarding the condition (1), $f_{s1}/f_w$ gets larger than or equal to 50 (the value of the right term), the angle of view needs to be narrowed in order to suppress the aberration caused in the first lens group G1 to an appropriate amount.

When, regarding the condition (1), $f_{s1}/f_w$ gets smaller than or equal to 20 (the value of the left term), the positive power becomes too strong in the first lens group G1 and therefore the effective diameter of the negative lens in the first lens group G1 needs to be increased in order to suppress the aberration caused in the first lens group G1 to an appropriate amount.

When considering usability of the electronic scope 1 for observing a body cavity, it is preferable that the best object distance becomes shorter as the focal length gets closer from the wide angle end to the telephoto end, and becomes shortest when the focal length reaches the telephoto end. By satisfying the condition (2), change of the object distance with respect to the observation magnification becomes appropriate. Furthermore, the observation magnification can be adequately secured.

When, regarding the condition (2), $f_t/f_w$ gets larger than equal to 1.5, the value of the right term, change of F number according to change of the magnification becomes too large and thereby resolution at the telephoto end decreases.

When, regarding the condition (2), $f_t/f_w$ gets smaller than equal to 1.2, the value of the left term, the magnification at the telephoto end becomes too small and thereby the adequate observation by an operator becomes difficult.

It should be noted that when the focal length of the first lens group G1 is defined as $f_1$ (unit: mm), the condition (1) may be replaced with the following condition (3):

$$5 < |f_{s1}/f_1| < 20 \quad (3)$$

When the conditions (2) and (3) are satisfied, the same advantageous effects as those achieved by satisfying the conditions (1) and (2) can be achieved.

When the focal length of the second lens group G2 is defined as $f_2$ (unit: mm), the variable power optical system 100 for an endoscope is configured to satisfy the following condition (4):

$$2 < f_2/f_w < 5 \quad (4)$$

By satisfying the condition (4), it becomes possible to secure the moving amount of the second lens group G2 required for the variable power while suppressing the entire length of the variable power optical system 100 for an endoscope.

When, regarding the condition (4), $f_2/f_w$ gets larger than equal to 5, the value of the right term, the power of the second lens group G2 becomes too small, and thereby the moving amount of the second lens group G2 required for the variable power becomes large and the entire length of the variable power optical system 100 for an endoscope becomes large. As a result, it becomes necessary to lengthen the entire length of the tip portion 12 of the electronic scope 1 being the rigid part in order to accommodate the variable power optical system 100 for an endoscope having the long entire length. Furthermore, when, regarding the condition (4), $f_2/f_w$ gets larger than equal to 5, the value of the right term, the observation magnification becomes too high, and thereby the operability of the electronic scope 1 when the observation is conducted at the telephoto end decreases. For example, in the observation, the tip portion 12 of the electronic scope 1 moves largely in response to a slight operation, and therefore it becomes difficult for the operator to bring an area which the operator wants to observe within the angle of view.

When, regarding the condition (4), $f_2/f_w$ gets smaller than equal to 2, the value of the left term, the power of the second lens group G2 becomes too strong, and therefore Petzval's sum becomes large in the negative direction and the curvature of filed occurs largely although the moving amount of the second lens group G2 required for the variable power can be suppressed.

When the focal length of the third lens group G3 is defined as $f_3$ (unit: mm), the variable power optical system 100 for an endoscope is configured to satisfy the following condition (5):

$$5 < f_3/f_w < 20 \qquad (5)$$

By satisfying the condition (5), the exit angle of light proceeding from the variable power optical system 100 for an endoscope to the solid-state image pickup device can be suppressed over the region from the wide angle end to the telephoto end.

When, regarding the condition (5), $f_3/f_w$ gets larger than equal to 20, the value of the right term, the power of the third lens group G3 becomes weak and thereby change of the exit angle of light according to the variable power becomes small whereas coma and chromatic aberration occur largely.

When, regarding the condition (5), $f_3/f_w$ gets smaller than equal to 5, the value of the left term, the power of the third lens group G3 becomes too large and thereby change of the exit angle of light according to the variable power becomes large.

The variable power optical system 100 for an endoscope is configured to satisfy the following condition (6):

$$-4 < f_1/f_w < -2 \qquad (6)$$

By satisfying the condition (6), the effective diameter of the first lens group G1 can be suppressed.

When, regarding the condition (6), $f_1/f_w$ gets larger than equal to −2, the value of the right term, power of the negative lens disposed on the most object side in the first lens group G1 becomes too strong, and therefore coma is caused largely.

When, regarding the condition (6), $f_1/f_w$ gets smaller than equal to −4, the value of the left term, it becomes necessary to increase the effective diameter of the negative lens disposed on the most object side in the first lens group G1 to secure a negative power of the first lens group G1.

Hereafter, five concrete numerical examples of the variable power optical system 100 for an endoscope described above will be explained. The variable power optical system 100 for an endoscope according each of the numerical examples 1 to 5 is disposed in the tip portion 12 of the electronic scope 1 shown in FIG. 1.

EXAMPLE 1

As described above, the variable power optical system 100 for an endoscope according to the example 1 has the configuration shown in FIG. 2.

Table 1 shows a concrete numerical configuration (design values) of the variable power optical system 100 for an endoscope (and the components disposed on the rear side thereof) according to the example 1. The surface number NO indicated in the top filed (surface data) in Table 1 corresponds to the surface reference rn (n: natural number) in FIG. 2, excepting the surface number 7 for the aperture stop S. In the top field of Table 1, R (unit: mm) denotes the radius of curvature of each surface of an optical component, D (unit: mm) denotes a thickness of an optical component or an interval between optical components on the optical axis, N(d) denotes a refractive index at d-line (wavelength of 588 nm), and vd denotes Abbe number at d-line.

The lower field (various data) of Table 1 shows, for each of the wide angle end and the telephoto end, specifications (the effective F number, the focal length (unit: mm) of the entire system, the optical magnification, the half angle of view (unit: degree), the image height (unit: mm), the group interval D6 (unit: mm), the group interval D12 (unit: mm)) of the variable power optical system 100 for an endoscope. The group interval D6 represents an interval between the first lens group G1 and the second lens group G2. The group interval D12 represents an interval between the second lens group G2 and the third lens group G3. Each of the group intervals D6 and D12 change depending on the position of the variable power.

TABLE 1

Example 1

Surface Data

| NO | R | D | N(d) | vd |
|---|---|---|---|---|
| 1 | INFINITY | 0.376 | 1.88300 | 40.8 |
| 2 | 1.359 | 0.397 | | |
| 3 | −44.859 | 0.381 | 1.62041 | 60.3 |
| 4 | −5.196 | 0.188 | | |
| 5 | −1.552 | 0.984 | 1.84666 | 23.8 |
| 6 | −1.863 | 1.380 | | |
| Aperture Stop 7 | INFINITY | 0.124 | | |
| 8 | 1.905 | 0.839 | 1.83481 | 42.7 |
| 9 | 2.912 | 0.202 | | |
| 10 | 10.082 | 0.282 | 1.84666 | 23.8 |
| 11 | 1.540 | 0.547 | 1.69680 | 55.5 |
| 12 | −2.638 | 0.143 | | |
| 13 | 2.128 | 0.282 | 1.92286 | 18.9 |
| 14 | 1.339 | 0.340 | | |
| 15 | 1.962 | 0.566 | 1.77250 | 49.6 |
| 16 | 13.264 | 0.620 | | |
| 17 | INFINITY | 0.939 | 1.51407 | 73.4 |
| 18 | INFINITY | 0.282 | 1.51000 | 64.1 |
| 19 | INFINITY | — | | |

Various Data

| | Wide Angle | Telephoto |
|---|---|---|
| F Number | 5.7 | 7.4 |
| Focal Length | 1.04 | 1.47 |
| Magnification | −0.101 | −0.539 |
| Half Angle of View | 74.8 | 38.9 |
| Image Height | 1.10 | 1.10 |

TABLE 1-continued

| Example 1 | | |
|---|---|---|
| D6 | 1.380 | 0.028 |
| D12 | 0.143 | 1.495 |

Figure 3:
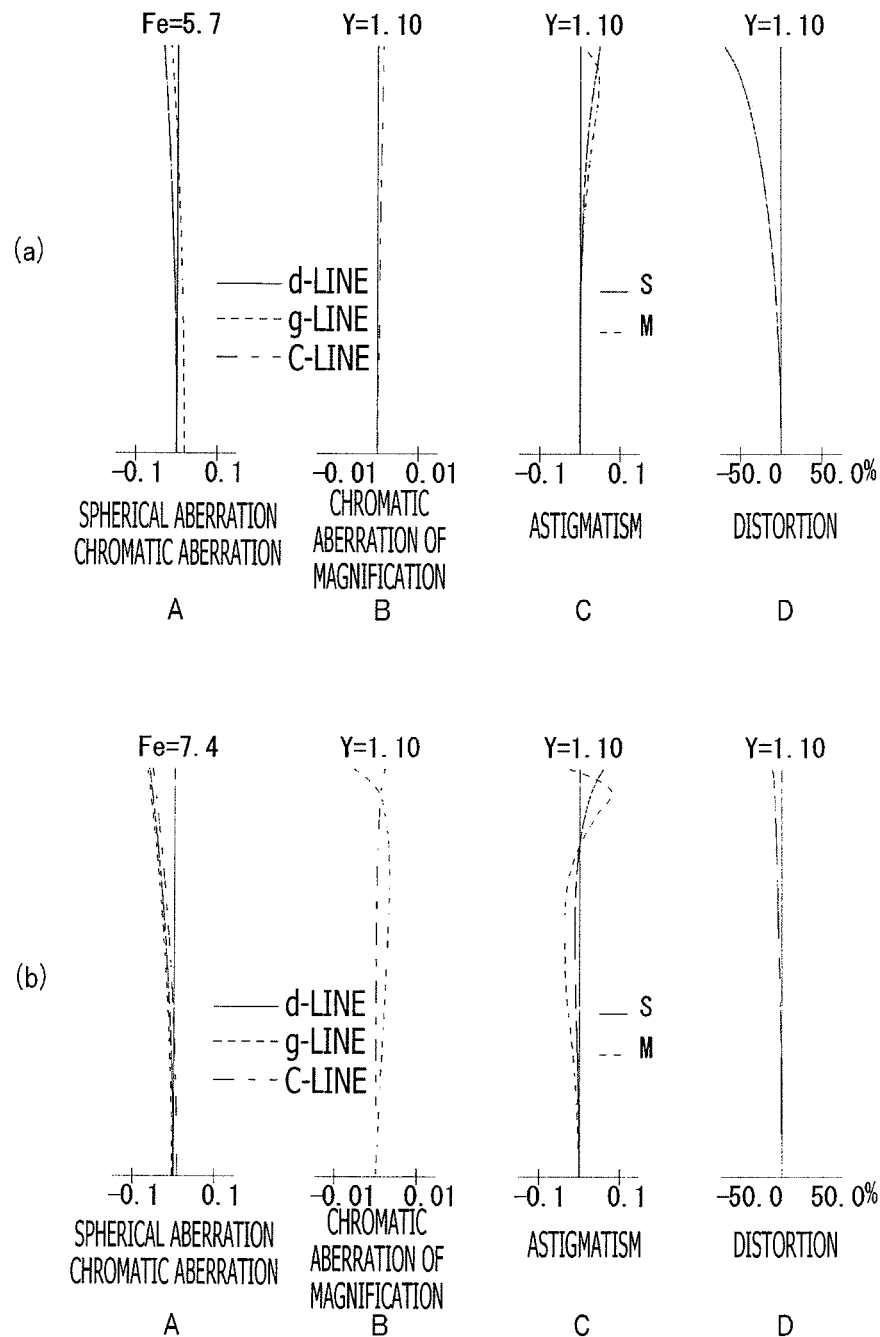
FIG. 3 illustrates various aberration diagrams of the variable power optical system for an endoscope according to the example 1 of the invention.

Graphs A to D in FIG. 3 (a) are various aberration diagrams of the variable power optical system 100 for an endoscope when the position of the variable power is at the wide angle end. Graphs A to D in FIG. 3 (b) are various aberration diagrams of the variable power optical system 100 for an endoscope when the position of the variable power is at the telephoto end. The graph A in each of FIGS. 3(a) and 3(b) represents the spherical aberration and the longitudinal chromatic aberration at d-line, g-line (the wavelength of 436 nm), and C-line (the wavelength of 656 nm). The graph B in each of FIGS. 3(a) and 3(b) represents the chromatic aberration of magnification at d-line, g-line and C-line. In each of the graphs A and B, a solid line represents the aberration at d-line, a dotted line represents the aberration at g-line and a chain line represents the aberration at C-line. The graph C in each of FIGS. 3(a) and 3(b) represents astigmatism. In the graph C, a solid line represents a sagittal component, and a dotted line represents a meridional component. The graph D in each of FIGS. 3(a) and 3(b) represents the distortion. In each of the graphs A to C, the vertical axis represents the image height, and the lateral axis represents the amount of aberration. In the graph D, the vertical axis represents the image height, and the lateral axis represents the distortion. The explanations about the tables and the drawings in the example 1 also apply to tables and drawings presented in the following numerical examples.

Since the effective diameter of the lens L1 is suppressed, the variable power optical system 100 for an endoscope according to the example 1 is configured such that the size in the radial direction of the entire variable power optical system 100 for an endoscope is suppressed (see Table 1). Furthermore, since the aberrations are corrected at each of the wide angle end and the telephoto end (see FIG. 3), and at least a positive lens having a convex surface pointing to the object side is provided as the third lens group G3 (see FIG. 2 and Table 1), the exit angle of light proceeding from the variable power optical system 100 for an endoscope to the solid-state image pickup device is suppressed. Furthermore, the adequate magnification for observation is secured (see Table 1). It should be noted that, in the intermediate region between the wide angle end and the telephoto end, the aberrations vary within the range shown in FIGS. 3(a) and 3(b). That is, the variable power optical system 100 for an endoscope according to the example 1 has suitable optical performance at every variable power position from the wide angle end to the telephoto end.

EXAMPLE 2

Each of FIGS. 4(a) and 4(b) is a cross sectional view illustrating arrangement of optical components including the variable power optical system 100 for an endoscope according to the example 2. FIG. 4(a) illustrates the lens arrangement when the position of the variable power is at the wide angle end. FIG. 4(b) illustrates the lens arrangement when the position of the variable power is at the telephoto end.

Graphs A to D in FIG. 5(a) are aberration diagrams illustrating the various aberrations when the position of the variable power is at the wide angle end in the variable power optical system 100 for an endoscope according to the example 2. Graphs A to D in FIG. 5(b) are aberration diagrams illustrating the various aberrations when the position of the variable power is at the telephoto end in the variable power optical system 100 for an endoscope according to the example 2.

Table 2 shows a concrete numerical configuration and specifications of the optical components including the variable power optical system 100 for an endoscope according to the example 2. In Table 2, the interval between the second lens group G2 and the third lens group G3 is represented by the symbol "D14".

TABLE 2

| Example 2 | | | | |
|---|---|---|---|---|
| Surface Data | | | | |
| NO | R | D | N(d) | vd |
| 1 | INFINITY | 0.358 | 1.88300 | 40.8 |
| 2 | 1.341 | 0.344 | | |
| 3 | −15.373 | 0.433 | 1.59270 | 35.3 |
| 4 | −3.355 | 0.260 | | |
| 5 | −1.113 | 0.727 | 1.77250 | 49.6 |
| 6 | −1.374 | D6 | | |
| Aperture Stop 7 | INFINITY | 0.109 | | |
| 8 | 1.315 | 0.856 | 1.88300 | 40.8 |
| 9 | 1.231 | 0.212 | | |
| 10 | 5.476 | 0.269 | 1.84666 | 23.8 |
| 11 | 1.030 | 0.599 | 1.77250 | 49.6 |
| 12 | −1.845 | 0.053 | | |
| 13 | −3.990 | 0.269 | 1.76182 | 26.5 |
| 14 | −8.437 | D14 | | |
| 15 | 3.615 | 0.388 | 1.51742 | 52.4 |
| 16 | INFINITY | 0.622 | | |
| 17 | INFINITY | 0.896 | 1.51407 | 73.4 |
| 18 | INFINITY | 0.269 | 1.51000 | 64.1 |
| 19 | INFINITY | — | | |

| Various Data | | |
|---|---|---|
| | Wide Angle | Telephoto |
| F Number | 10.2 | 13.1 |
| Focal Length | 1.00 | 1.39 |
| Magnification | −0.102 | −0.543 |
| Half Angle of View | 74.2 | 41.1 |
| Image Height | 1.05 | 1.05 |
| D6 | 1.244 | 0.027 |
| D14 | 0.081 | 1.298 |

Figure 4:
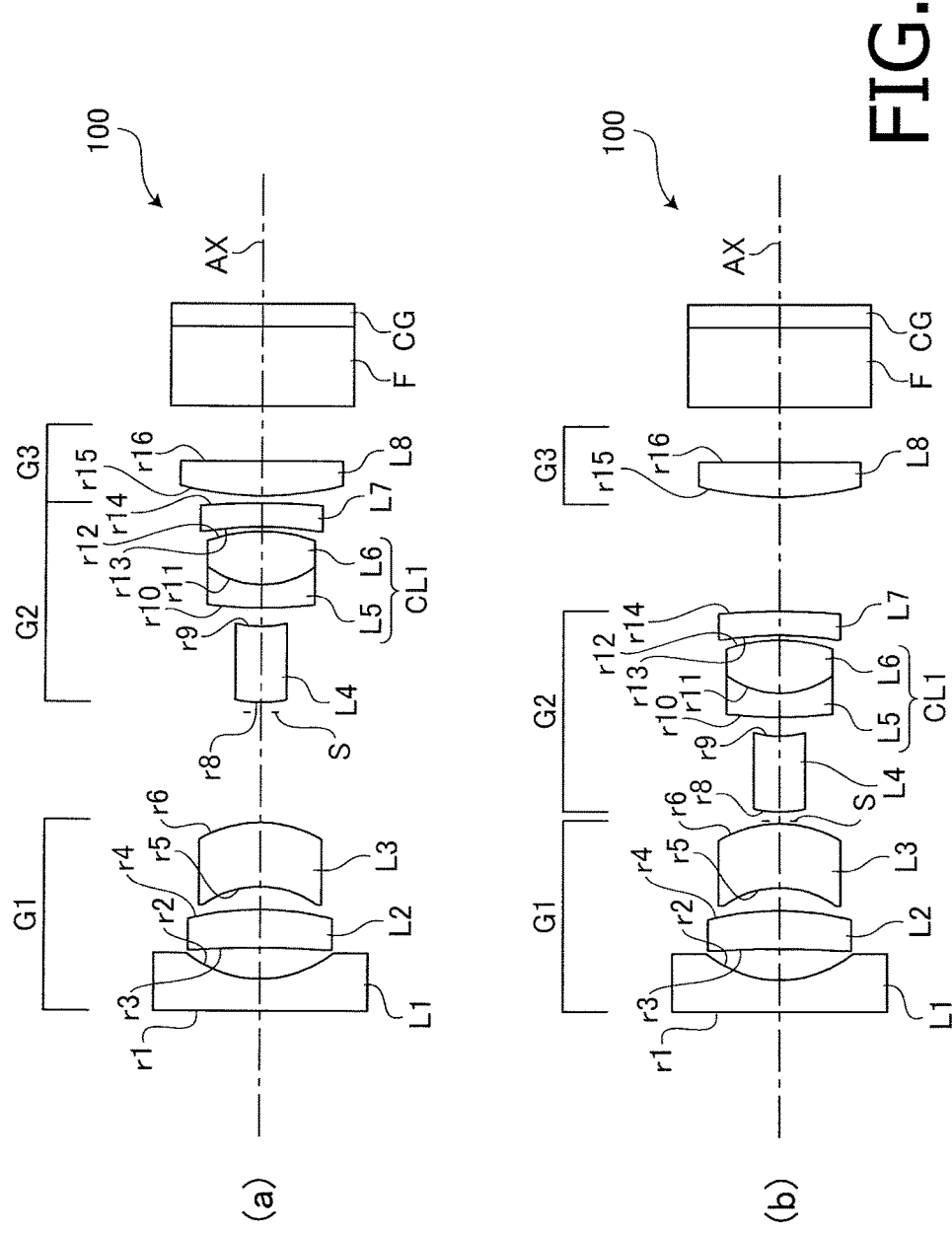
FIG. 4 is a lens arrangement diagram illustrating a configuration of a variable power optical system for an endoscope according to an example 2 of the invention.
Figure 5:
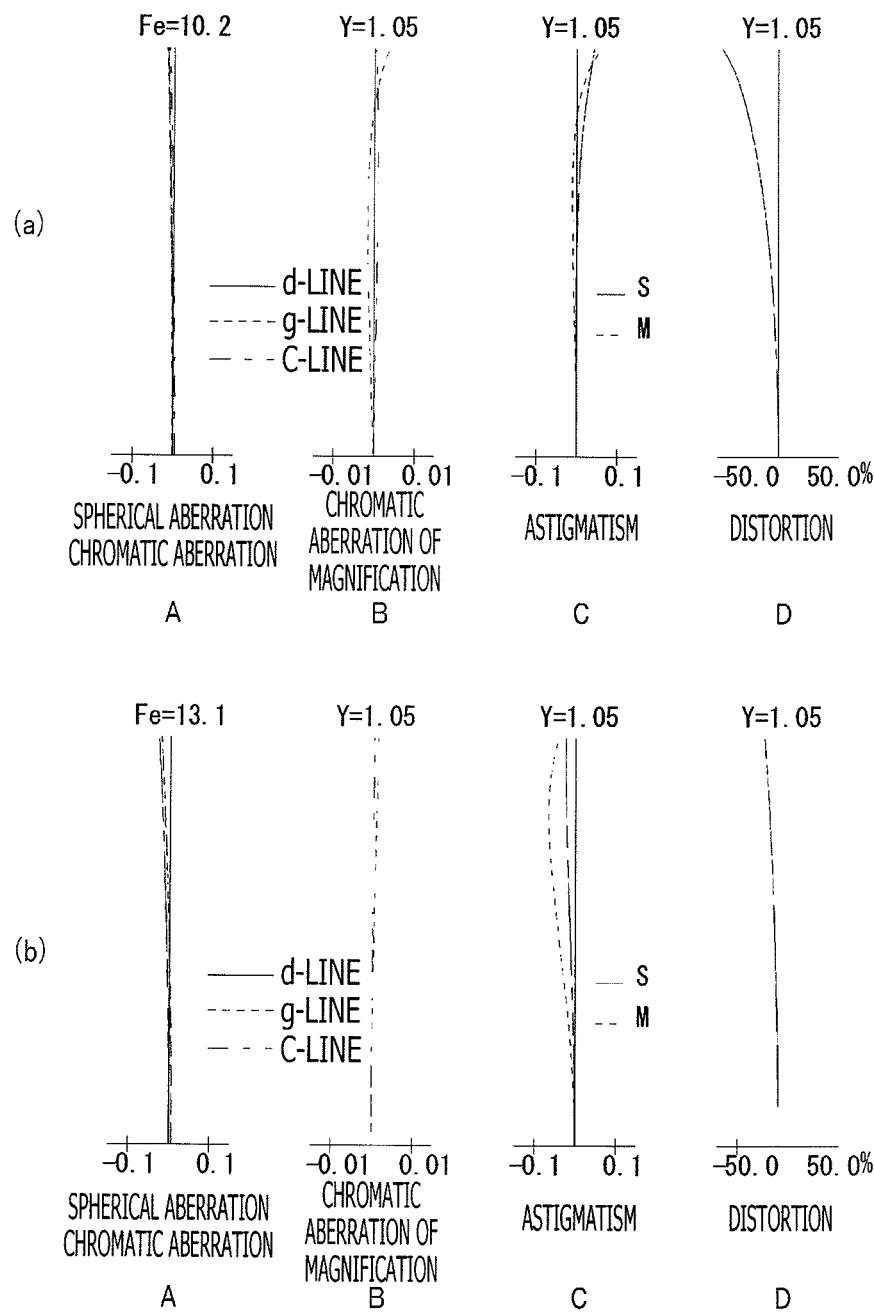
FIG. 5 illustrates various aberration diagrams of the variable power optical system for an endoscope according to the example 2 of the invention.

As can be seen from FIGS. 4 and 5 and Table 2, the variable power optical system 100 for an endoscope according to the example 2 is configured such that the size in the radial direction of the entire optical system is suppressed, and that the adequate magnification for observation is secured, the suitable optical performance is secured over the range from the wide angle end to the telephoto end and the exit angle of light proceeding from the variable power optical system 100 for an endoscope to the solid-state image, pickup device is suppressed.

EXAMPLE 3

Each of FIGS. 6(a) and 6(b) is a cross sectional view illustrating arrangement of optical components including the variable power optical system 100 for an endoscope according to the example 3. FIG. 6(a) illustrates the lens arrangement when the position of the variable power is at the wide angle end. FIG. 6(b) illustrates the lens arrangement when the position of the variable power is at the telephoto end.

Graphs A to D in FIG. 7(a) are aberration diagrams illustrating the various aberrations when the position of the variable power is at the wide angle end in the variable power optical system 100 for an endoscope according to the example 3. Graphs A to D in FIG. 7(b) are aberration diagrams illustrating the various aberrations when the position of the variable power is at the telephoto end in the variable power optical system 100 for an endoscope according to the example 3.

Table 3 shows a concrete numerical configuration and specifications of the optical components including the variable power optical system 100 for an endoscope according to the example 3. In Table 3, the interval between the second lens group G2 and the third lens group G3 is represented by the symbol "D14".

TABLE 3

Example 3

Surface Data

| NO | R | D | N(d) | vd |
|---|---|---|---|---|
| 1 | INFINITY | 0.341 | 1.88300 | 40.8 |
| 2 | 1.297 | 0.370 | | |
| 3 | −11.970 | 0.386 | 1.59270 | 35.3 |
| 4 | −3.153 | 0.291 | | |
| 5 | −1.003 | 0.619 | 1.77250 | 49.6 |
| 6 | −1.238 | D6 | | |
| Aperture Stop 7 | INFINITY | 0.105 | | |
| 8 | 1.254 | 0.817 | 1.88300 | 40.8 |
| 9 | 1.227 | 0.199 | | |
| 10 | 5.125 | 0.256 | 1.84666 | 23.8 |
| 11 | 0.922 | 0.543 | 1.77250 | 49.6 |
| 12 | −2.153 | 0.065 | | |
| 13 | −6.885 | 0.256 | 1.84666 | 23.8 |
| 14 | −10.262 | D14 | | |
| 15 | 3.747 | 0.353 | 1.51742 | 52.4 |
| 16 | INFINITY | 0.589 | | |
| 17 | INFINITY | 0.852 | 1.51407 | 73.4 |
| 18 | INFINITY | 0.256 | 1.51000 | 64.1 |
| 19 | INFINITY | — | | |

Various Data

| | Wide Angle | Telephoto |
|---|---|---|
| F Number | 6.9 | 8.9 |
| Focal Length | 0.96 | 1.32 |
| Magnification | −0.102 | −0.551 |
| Half Angle of View | 74.4 | 35.5 |
| Image Height | 1.00 | 0.89 |
| D6 | 1.235 | 0.094 |
| D14 | 0.085 | 1.227 |

Figure 6:
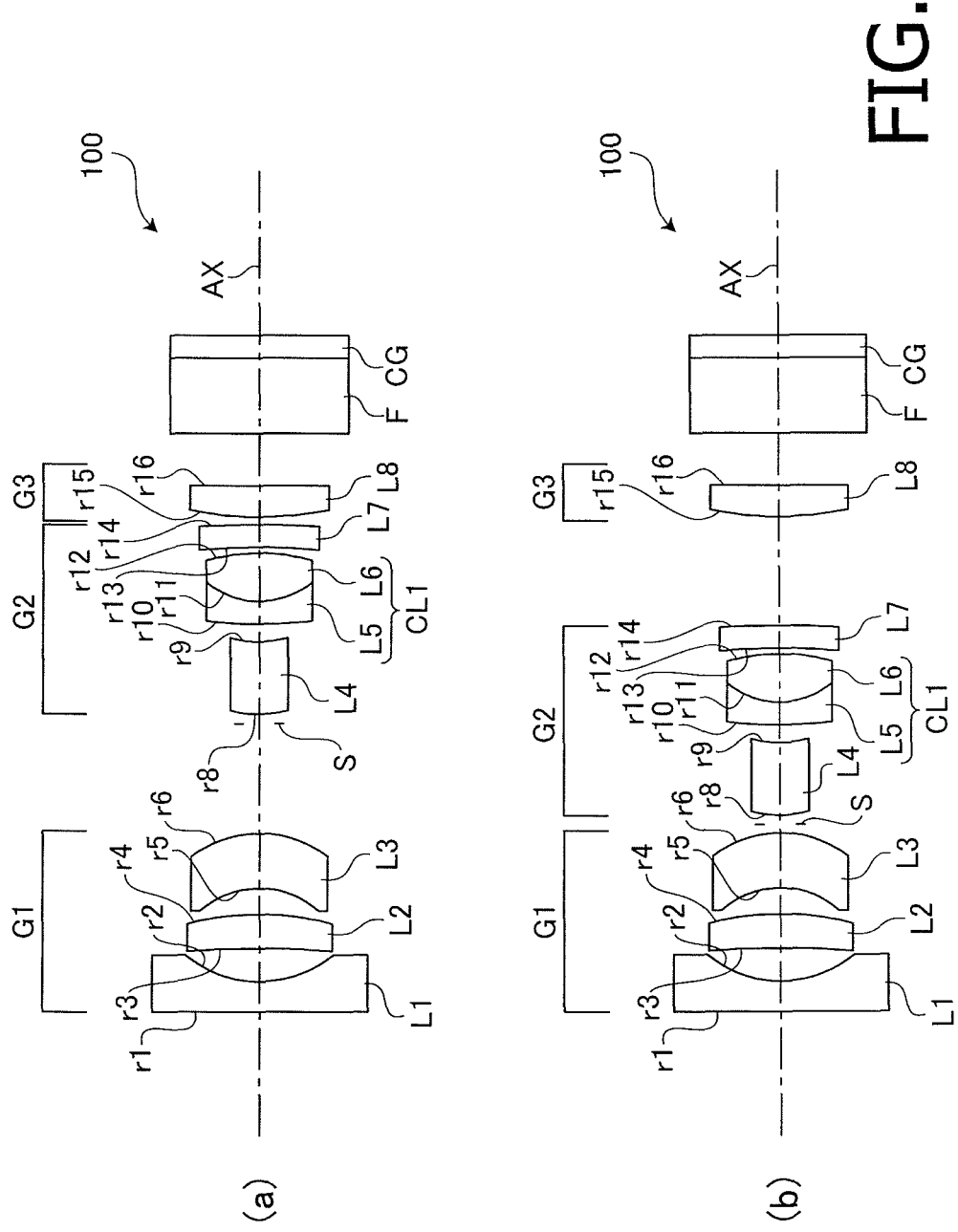
FIG. 6 is a lens arrangement diagram illustrating a configuration of a variable power optical system for an endoscope according to an example 3 of the invention.
Figure 7:
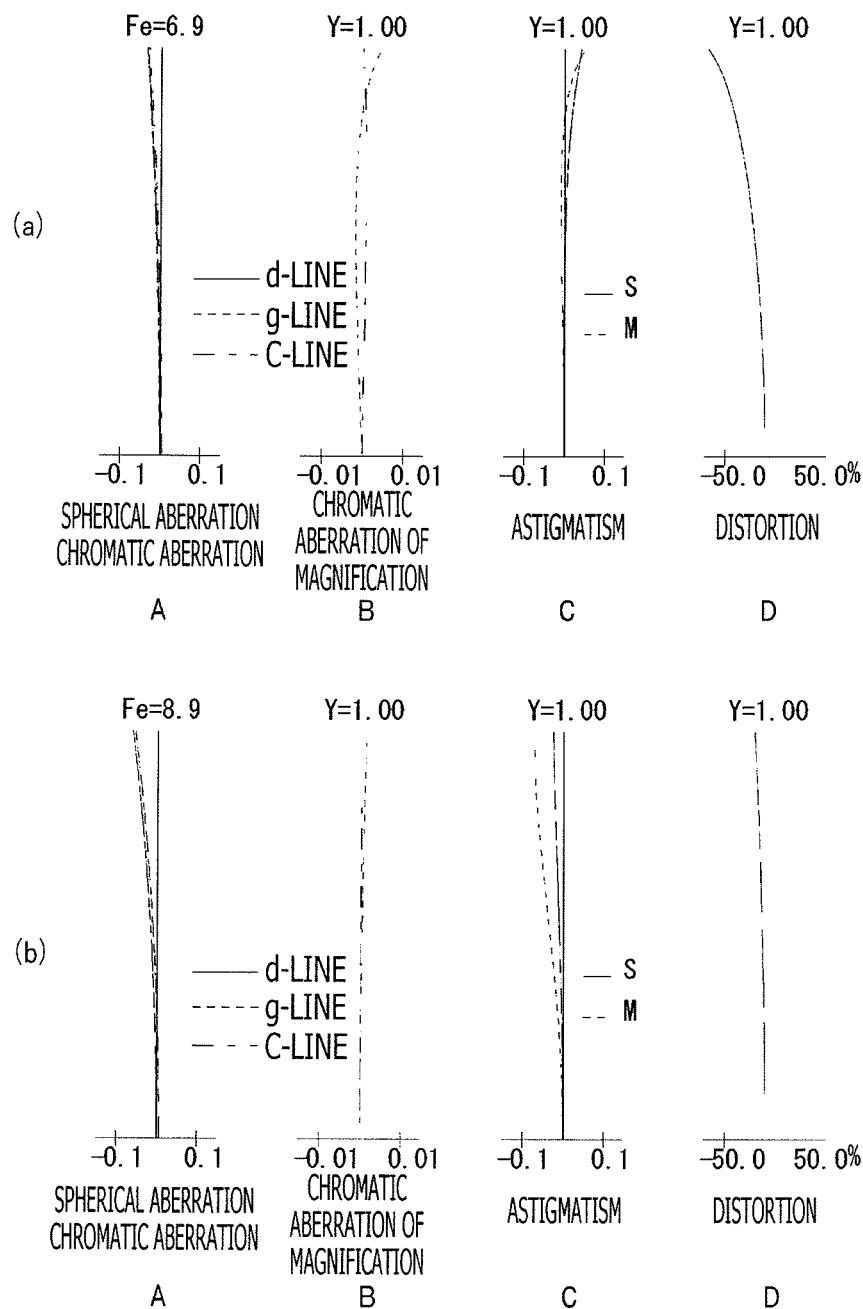
FIG. 7 illustrates various aberration diagrams of the variable power optical system for an endoscope according to the example 3 of the invention.

As can be seen from FIGS. 6 and 7 and Table 3, the variable power optical system 100 for an endoscope according to the example 3 is configured such that the size in the radial direction of the entire optical system is suppressed, and that the adequate magnification for observation is secured, the suitable optical performance is secured over the range from the wide angle end to the telephoto end and the exit angle of light proceeding from the variable power optical system 100 for an endoscope to the solid-state image pickup device is suppressed.

EXAMPLE 4

Each of FIGS. 8(a) and 8(b) is a cross sectional view illustrating arrangement of optical components including the variable power optical system 100 for an endoscope according to the example 4. FIG. 8(a) illustrates the lens arrangement when the position of the variable power is at the wide angle end. FIG. 8(b) illustrates the lens arrangement when the position of the variable power is at the telephoto end.

Graphs A to D in FIG. 9(a) are aberration diagrams illustrating the various aberrations when the position of the variable power is at the wide angle end in the variable power optical system 100 for an endoscope according to the example 4. Graphs A to D in FIG. 9(b) are aberration diagrams illustrating the various aberrations when the position of the variable power is at the telephoto end in the variable power optical system 100 for an endoscope according to the example 4.

Table 4 shows a concrete numerical configuration and specifications of the optical components including the variable power optical system 100 for an endoscope according to the example 4. In Table 4, the interval between the first lens group G1 and the second lens group G2 is represented by the symbol "D4", and the interval between the second lens group G2 and the third lens group G3 is represented by the symbol "D12".

TABLE 4

Example 4

Surface Data

| NO | R | D | N(d) | vd |
|---|---|---|---|---|
| 1 | INFINITY | 0.340 | 1.88300 | 40.8 |
| 2 | 1.876 | 0.614 | | |
| 3 | −1.361 | 0.847 | 1.88300 | 40.8 |
| 4 | −1.636 | D4 | | |
| Aperture Stop 5 | INFINITY | 0.111 | | |
| 6 | 1.592 | 0.695 | 1.88300 | 40.8 |
| 7 | 1.465 | 0.315 | | |
| 8 | −4.358 | 0.434 | 1.80400 | 46.6 |
| 9 | −1.471 | 0.131 | | |
| 10 | 12.713 | 0.548 | 1.88300 | 40.8 |
| 11 | −1.853 | 0.255 | 1.95906 | 17.5 |
| 12 | −14.011 | D12 | | |
| 13 | 2.509 | 0.441 | 1.72916 | 54.7 |
| 14 | 4.185 | 0.618 | | |
| 15 | INFINITY | 0.850 | 1.51407 | 73.4 |
| 16 | INFINITY | 0.255 | 1.51000 | 64.1 |
| 17 | INFINITY | — | | |

Various Data

| | Wide Angle | Telephoto |
|---|---|---|
| F Number | 8.2 | 9.7 |
| Focal Length | 1.00 | 1.28 |
| Magnification | −0.106 | −0.460 |
| Half Angle of View | 75.9 | 46.4 |
| Image Height | 1.00 | 1.00 |
| D4 | 1.030 | 0.085 |
| D12 | 0.116 | 1.062 |

Figure 8:
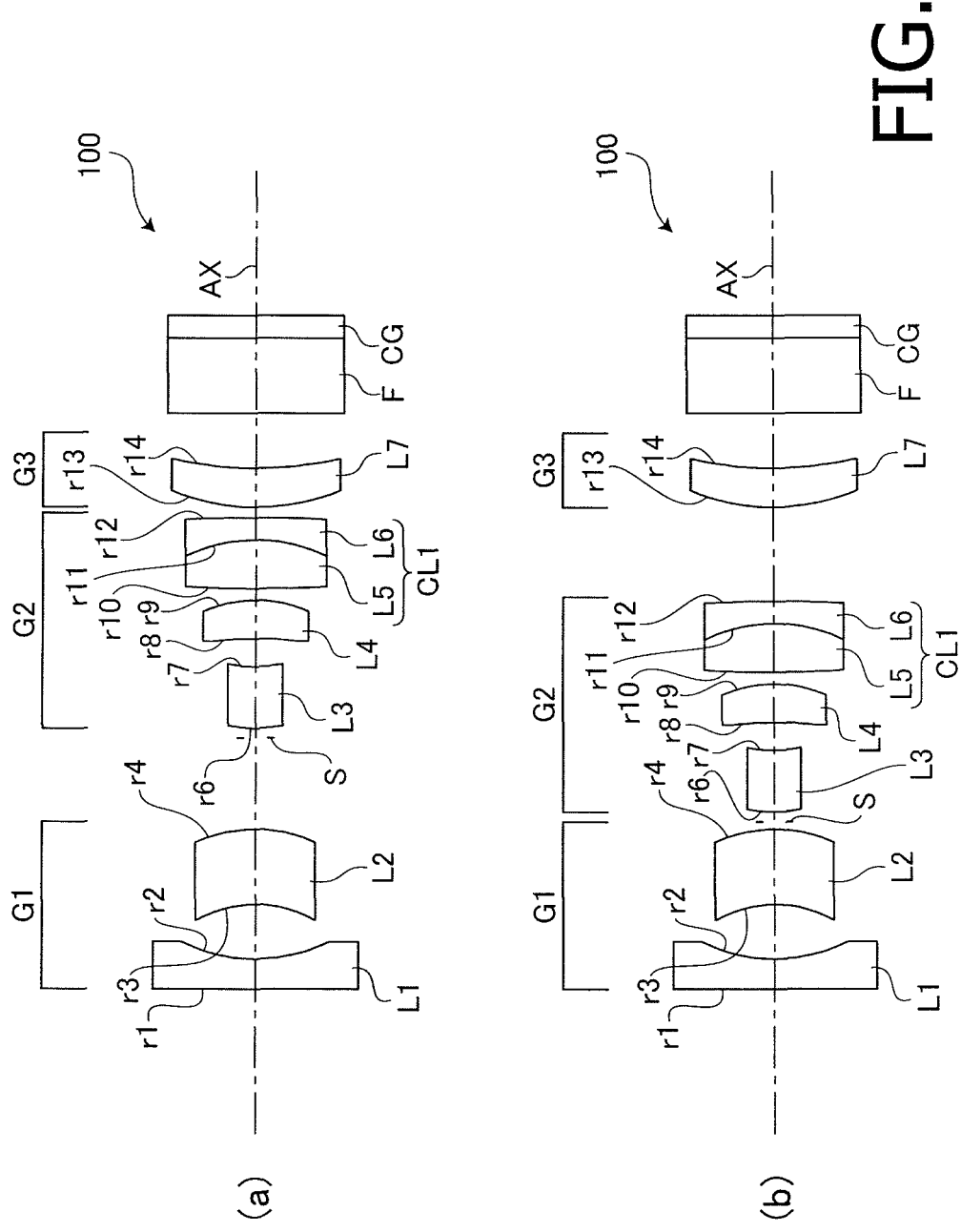
FIG. 8 is a lens arrangement diagram illustrating a configuration of a variable power optical system for an endoscope according to an example 4 of the invention.
Figure 9:
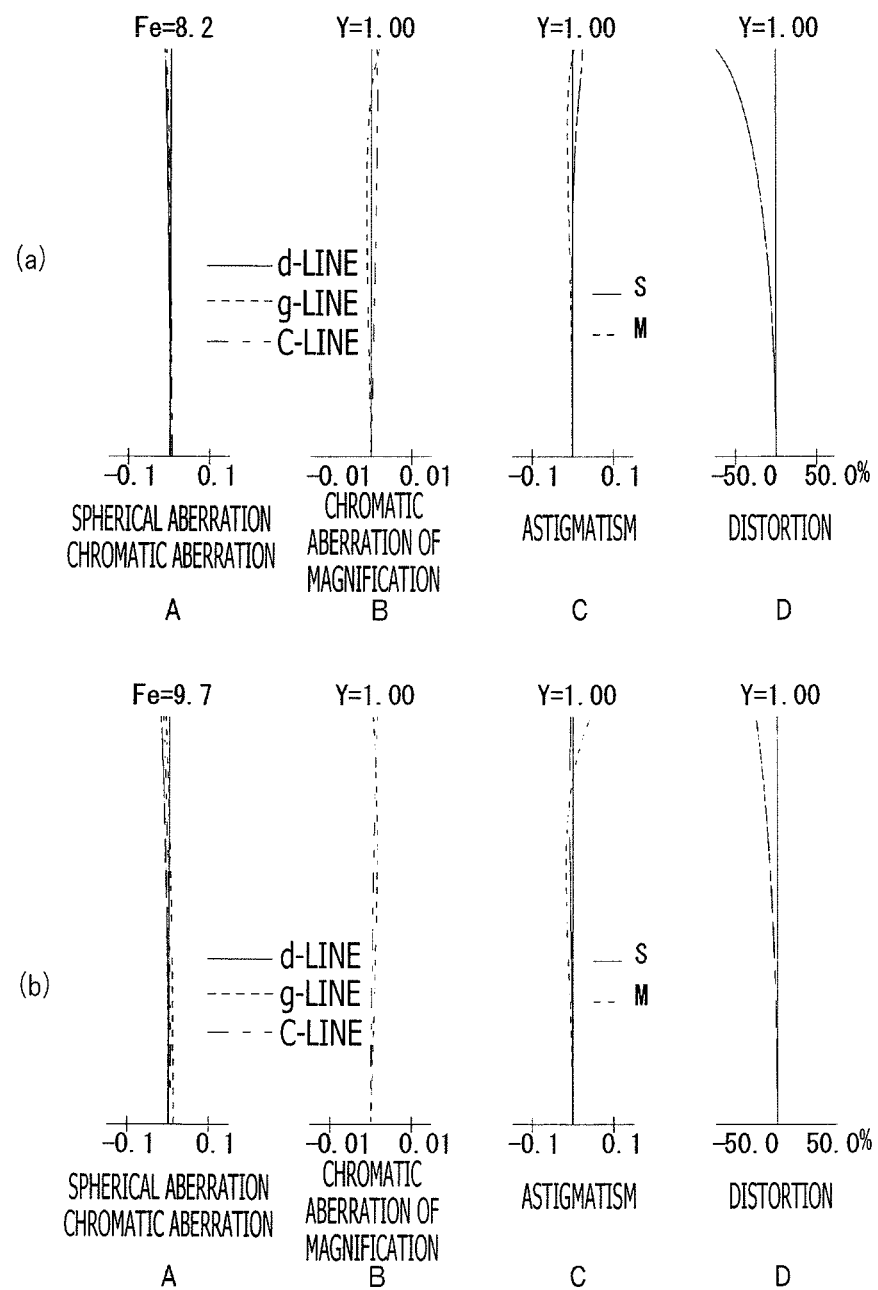
FIG. 9 illustrates various aberration diagrams of the variable power optical system for an endoscope according to the example 4 of the invention.

As can be seen from FIGS. 8 and 9 and Table 4, the variable power optical system 100 for an endoscope according to the example 4 is configured such that the size in the radial direction of the entire optical system is suppressed, and that the adequate magnification for observation is secured, the suitable optical performance is secured over the range from the wide angle end to the telephoto end and the exit angle of light proceeding from the variable power optical system 100 for an endoscope to the solid-state image pickup device is suppressed.

EXAMPLE 5

Figure 10:
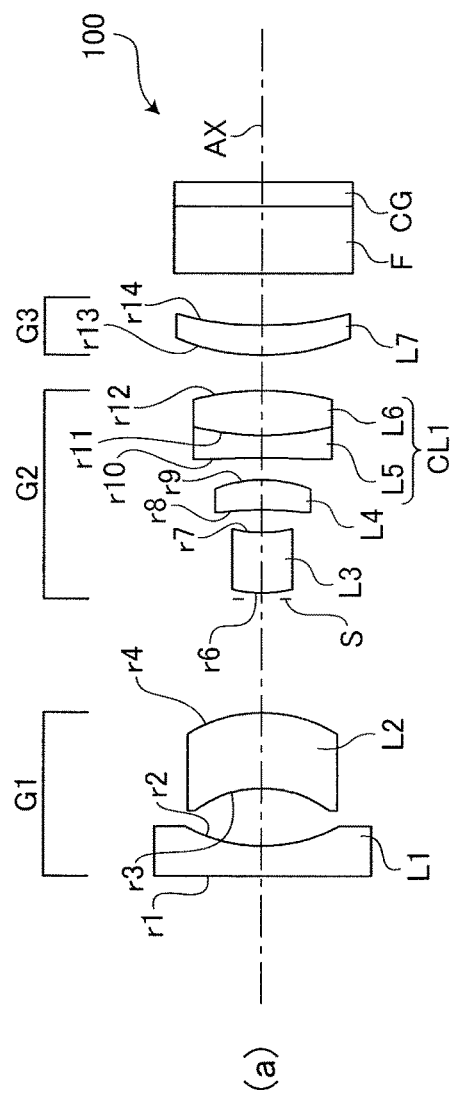
FIG. 10 is a lens arrangement diagram illustrating a configuration of a variable power optical system for an endoscope according to an example 5 of the invention.
Figure 10:
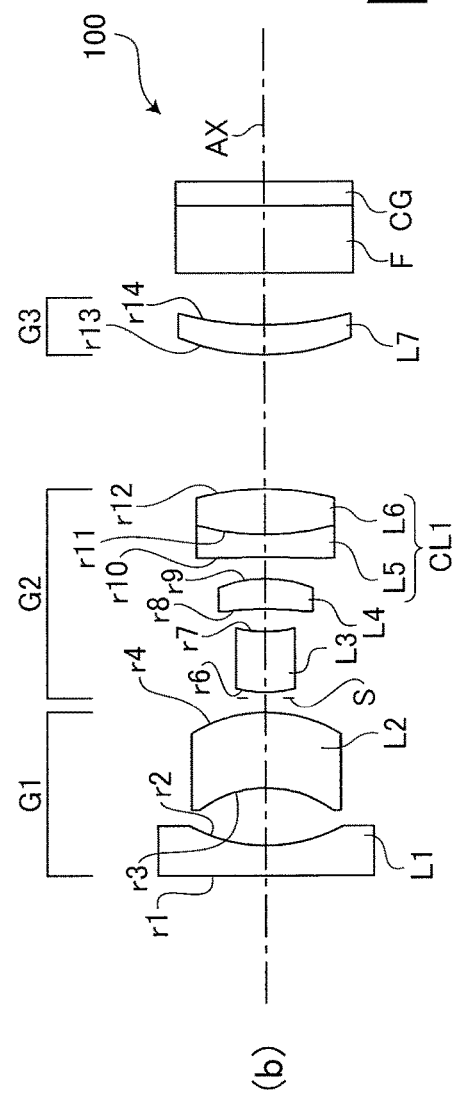

Each of FIGS. 10(a) and 10(b) is a cross sectional view illustrating arrangement of optical components including the variable power optical system 100 for an endoscope according to the example 5. FIG. 10(a) illustrates the lens arrangement when the position of the variable power is at the wide angle end. FIG. 10(*b*) illustrates the lens arrangement when the position of the variable power is at the telephoto end.

Figure 11:
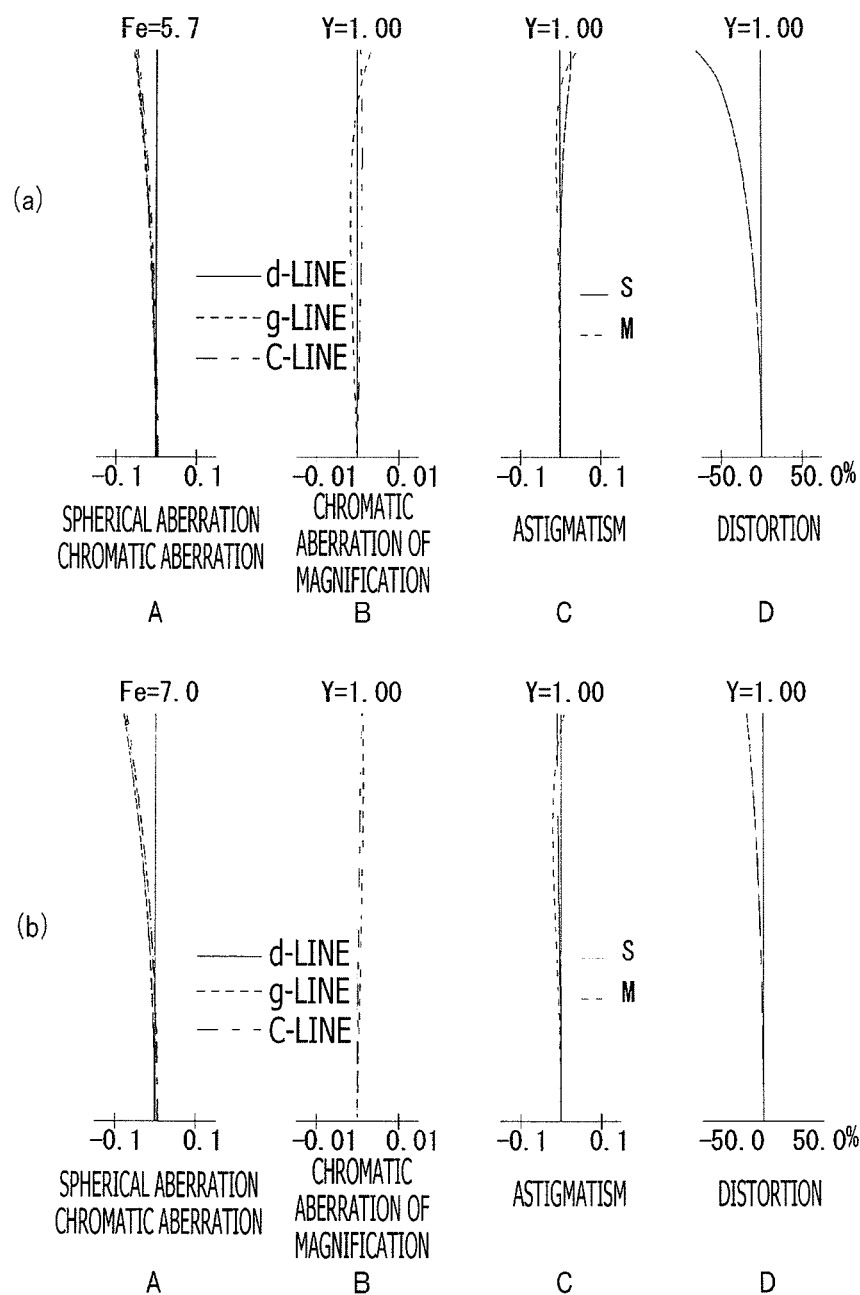
FIG. 11 illustrates various aberration diagrams of the variable power optical system for an endoscope according to the example 5 of the invention.

Graphs A to D in FIG. 11(*a*) are aberration diagrams illustrating the various aberrations when the position of the variable power is at the wide angle end in the variable power optical system 100 for an endoscope according to the example 5. Graphs A to D in FIG. 11(*b*) are aberration diagrams illustrating the various aberrations when the position of the variable power is at the telephoto end in the variable power optical system 100 for an endoscope according to the example 5.

Table 5 shows a concrete numerical configuration and specifications of the optical components including the variable power optical system 100 for an endoscope according to the example 5. In Table 5, the interval between the first lens group G1 and the second lens group G2 is represented by the symbol "D4", and the interval between the second lens group G2 and the third lens group G3 is represented by the symbol "D12".

TABLE 5

Example 5

Surface Data

| NO | R | D | N(d) | νd |
|---|---|---|---|---|
| 1 | INFINITY | 0.335 | 1.88300 | 40.8 |
| 2 | 1.819 | 0.637 | | |
| 3 | −1.257 | 0.838 | 1.88300 | 40.8 |
| 4 | −1.589 | D4 | | |
| Aperture Stop 5 | INFINITY | 0.067 | | |
| 6 | 1.427 | 0.670 | 1.88300 | 40.8 |
| 7 | 1.387 | 0.251 | | |
| 8 | −3.590 | 0.335 | 1.80400 | 46.6 |
| 9 | −1.410 | 0.243 | | |
| 10 | −12.863 | 0.251 | 1.95906 | 17.5 |
| 11 | 3.069 | 0.503 | 1.77250 | 49.6 |
| 12 | −3.069 | D12 | | |
| 13 | 2.546 | 0.335 | 1.72916 | 54.7 |
| 14 | 3.875 | 0.574 | | |
| 15 | INFINITY | 0.750 | 1.51407 | 73.4 |
| 16 | INFINITY | 0.270 | 1.51000 | 63.0 |
| 17 | INFINITY | — | | |

Various Data

| | Wide Angle | Telephoto |
|---|---|---|
| F Number | 5.7 | 7.0 |
| Focal Length | 0.99 | 1.32 |
| Magnification | −0.106 | −0.562 |
| Half Angle of View | 80.5 | 42.9 |
| Image Height | 1.00 | 1.00 |
| D4 | 1.274 | 0.167 |
| D12 | 0.396 | 1.502 |

As can be seen from FIGS. 10 and 11 and Table 5, the variable power optical system 100 for an endoscope according to the example 5 is configured such that the size in the radial direction of the entire optical system is suppressed, and that the adequate magnification for observation is secured, the suitable optical performance is secured over the range from the wide angle end to the telephoto end and the exit angle of light proceeding from the variable power optical system 100 for an endoscope to the solid-state image pickup device is suppressed.

Verification of Conditions

Table 6 shows a list of values obtained by applying the conditions (1) to (6) to the examples 1 to 5.

TABLE 6

(Verification for Conditions)

| | Example 1 | Example 2 | Example 3 | Example 4 | Example 5 |
|---|---|---|---|---|---|
| (1) $f_{s1}/f_w$ | 23.5 | 35.4 | 47.2 | 20.7 | 37.5 |
| (2) $f_1/f_w$ | 1.42 | 1.39 | 1.38 | 1.28 | 1.34 |
| (3) $|f_{s1}/f_1|$ | 7.68 | 10.85 | 15.15 | 6.10 | 12.21 |
| (4) $f_2/f_w$ | 2.57 | 2.50 | 2.44 | 2.33 | 2.33 |
| (5) $f_3/f_w$ | 7.42 | 6.99 | 7.57 | 7.73 | 9.33 |
| (6) $f_t/f_w$ | −3.06 | −3.26 | −3.11 | −3.40 | −3.07 |

As shown in Table 6, the variable power optical system 100 for an endoscope according to each of the examples 1 to 5 satisfies the conditions (1) and (2) (and conditions (1) and (3)). Consequently, the variable power optical system 100 for an endoscope according to each of the examples 1 to 5 is configured such that the size in the radial direction of the entire optical system is suppressed, and that the adequate magnification for observation is secured, and the suitable optical performance is secured over the range from the wide angle end to the telephoto end. Furthermore, the variable power optical system 100 for an endoscope according to each of the examples 1 to 5 satisfies the conditions (4) to (6). Therefore, in the examples 1 to 5, the advantageous effects attached by satisfying the conditions (4) to (6) are provided.

The foregoing is the explanation about the embodiment of the invention. The embodiment according to the invention is not limited to the above described embodiment, but can be varied in various ways within the scope of the invention. For example, embodiments according to invention include a combination of embodiments explicitly described in this specification and embodiments easily realized from the above described embodiment.

What is claimed is:

1. A variable power optical system for an endoscope, comprising a first lens group having a negative power, a second lens group having a positive power and a third lens group arranged in this order from an object side, variable power optical system for an endoscope being configured to change magnification for an optical image by moving the second lens group in a direction of an optical axis with respect to the first lens group and the third lens group which are fixed lens groups, while keeping a distance from a most object side lens surface of the first lens group to an image plane constant, the first lens group including at least a negative lens having a concave surface pointing to an image side and a positive meniscus lens having a concave surface pointing to the object side, arranged in this order from the object side, the second lens group including at least a meniscus lens having a convex surface pointing to the object side and a cemented lens formed by cementing together a negative lens and a positive lens, arranged in this order from the object side, the third lens group including at least a positive lens having a convex surface pointing to the object side, wherein, when a focal length of the meniscus lens which the first lens group includes is defined as $f_{s1}$ (unit: mm), an overall focal length of the first to third lens groups at wide angle end is defined as $f_w$ (unit: mm), and the overall focal length of the first to third lens groups at a telephoto end is defined as $f_t$ (unit: mm), the variable power optical system for an endoscope satisfies following two conditions:

$20 < f_{s1}/f_w < 50$ $1.2 < f_t/f_w < 1.5$.

2. A variable power optical system for an endoscope, comprising a first lens group having a negative power, a second lens group having a positive power and a third lens group arranged in this order from an object side, the variable power optical system for an endoscope being configured to change magnification for an optical image by moving the second lens group in a direction of an optical axis with respect to the first lens group and the third lens group which are fixed lens groups, while keeping a distance from a most object side lens surface of the first lens group to an image plane constant,
- the first lens group including at least a negative lens having a concave surface pointing to an image side and a positive meniscus lens having a concave surface pointing to the object side, arranged in this order from the object side,
- the second lens group including at least a meniscus lens having a convex surface pointing to the object side and a cemented lens formed by cementing together a negative lens and a positive lens, arranged in this order from the object side,
- the third lens group including at least a positive lens having a convex surface pointing to the object side,
- wherein, when a focal length of the meniscus lens which the first lens group includes is defined as $f_{s1}$ (unit: mm), a focal length of the first lens group is defined as $f_1$ (unit: mm), an overall focal length of the first to third lens groups at a wide angle end is defined as $f_w$ (unit: mm), and the overall focal length of the first to third lens groups at a telephoto end is defined as $f_t$ (unit: mm), the variable power optical system for an endoscope satisfies following two conditions:

$5<|f_{s1}/f_1|<20$ $1.2<f_t/f_w<1.5$.

3. The variable power optical system for an endoscope according to claim 1, wherein, when a focal length of the second lens group is defined as $f_2$ (unit: mm), the variable power optical system for an endoscope satisfies a following condition:

$2<f_2/f_w<5$.

4. The variable power optical system for an endoscope according to claim 1, wherein, when a focal length of the third lens group is defined as $f_3$ (unit: mm), the variable power optical system for an endoscope satisfies a following condition:

$5<f_3/f_w<20$.

5. The variable power optical system for an endoscope according to claim 1, wherein, when a focal length of the first lens group is defined as $f_1$ (unit: mm), the variable power optical system for an endoscope satisfies a following condition:

$-4<f_1/f_w<-2$.

6. The variable power optical system for an endoscope according to claim 1, further comprising an aperture stop disposed between the first lens group and the second lens group to move along the optical axis integrally with the second lens group.

7. The variable power optical system for an endoscope according to claim 1, wherein an angle of view of the variable power optical system for an endoscope is 120 degrees or more.

8. An endoscope comprising a variable power optical system for an endoscope according to claim 1, the variable power optical system for an endoscope is installed in a tip portion of the endoscope.

\* \* \* \* \*